(12) United States Patent
Weber et al.

(10) Patent No.: US 9,801,578 B2
(45) Date of Patent: Oct. 31, 2017

(54) REDUCED SIZE OPTICAL COUPLER FOR FLUORESCENCE DETECTION

(71) Applicant: Becton, Dickinson and Company, Franklin Lakes, NJ (US)

(72) Inventors: Aaron Weber, Arlington, MA (US); David Tracy, Champaign, IL (US); James Salemme, Billerica, MA (US); John Prudden, Manchester, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/762,447

(22) PCT Filed: Jan. 21, 2014

(86) PCT No.: PCT/US2014/012365
§ 371 (c)(1),
(2) Date: Jul. 21, 2015

(87) PCT Pub. No.: WO2014/116597
PCT Pub. Date: Jul. 31, 2014

(65) Prior Publication Data
US 2015/0351669 A1    Dec. 10, 2015

Related U.S. Application Data

(60) Provisional application No. 61/755,296, filed on Jan. 22, 2013.

(51) Int. Cl.
*A61B 5/1455* (2006.01)
*A61B 5/154* (2006.01)
(Continued)

(52) U.S. Cl.
CPC .......... *A61B 5/1545* (2013.01); *A61B 5/0071* (2013.01); *A61B 5/1459* (2013.01);
(Continued)

(58) Field of Classification Search
CPC . A61B 5/14532; A61B 5/1455; A61B 5/1495; A61B 5/1459; A61B 5/14546;
(Continued)

(56) References Cited

U.S. PATENT DOCUMENTS

| | | | |
|---|---|---|---|
| 5,341,805 A * | 8/1994 | Stavridi | A61B 5/0071 356/317 |
| 6,125,228 A | 9/2000 | Gong | |
| 7,991,290 B2 * | 8/2011 | Tanaka | G02B 6/4246 398/135 |
| 2004/0259270 A1 * | 12/2004 | Wolf | A61B 5/076 436/518 |

(Continued)

FOREIGN PATENT DOCUMENTS

| | | | |
|---|---|---|---|
| WO | WO-2009055705 A2 | 4/2009 | |
| WO | WO 2010134342 A1 * | 11/2010 | A61B 3/102 |

*Primary Examiner* — Eric Winakur
*Assistant Examiner* — Chu Chuan (JJ) Liu
(74) *Attorney, Agent, or Firm* — Dickinson Wright PLLC

(57) ABSTRACT

Optical systems are disclosed for use in identifying an analyte, such as glucose in blood or interstitial fluid (ISF), using a biomaterial, such as glucose binding protein (GBP), that is brought into contact with the analyte. An optical system includes a first filter adapted to reflect light emitted from a light-emitting diode to illuminate a fluorescent body, and further adapted to transmit light emitted from the fluorescent body, and a second filter adapted to separate light transmitted by the first filter into signal band light and reference band light.

20 Claims, 11 Drawing Sheets

(51) Int. Cl.
   *G01N 21/64*    (2006.01)
   *A61B 5/145*   (2006.01)
   *A61B 5/00*    (2006.01)
   *A61B 5/1459*  (2006.01)

(52) U.S. Cl.
   CPC ....... *A61B 5/14532* (2013.01); *G01N 21/645* (2013.01); *G01N 21/6486* (2013.01); *A61B 2562/0233* (2013.01); *G01N 2201/062* (2013.01); *G01N 2201/08* (2013.01)

(58) Field of Classification Search
   CPC ............ A61B 5/14551; A61B 5/14552; A61B 5/2562; G01N 21/645; G01N 21/6486; G01N 2021/6491
   See application file for complete search history.

(56) References Cited

U.S. PATENT DOCUMENTS

| | | |
|---|---|---|
| 2005/0113657 A1 | 5/2005 | Alarcon et al. |
| 2005/0113658 A1* | 5/2005 | Jacobson ........... A61B 5/14532 600/342 |
| 2006/0093262 A1* | 5/2006 | Matsumoto ........ G01N 21/7703 385/31 |
| 2007/0229696 A1* | 10/2007 | Mochizuki ........... G02B 21/361 348/340 |
| 2009/0116006 A1* | 5/2009 | Tokita ................. A61B 5/14532 356/300 |
| 2012/0100631 A1 | 4/2012 | Dillmore et al. |
| 2013/0006069 A1* | 1/2013 | Gil ....................... A61B 5/1459 600/316 |

* cited by examiner

REDUCED SIZE OPTICAL COUPLER FOR FLUORESCENCE DETECTION

CROSS-REFERENCE TO RELATED APPLICATION

This application claims the benefit under 35 U.S.C.§119(e) of U.S. Provisional Application No. 61/755,296, filed on Jan. 22, 2013, in the U.S. Patent and Trademark Office, the disclosure of which is incorporated herein by reference in its entirety.

FIELD OF THE INVENTION

The present invention relates generally to continuous glucose monitoring (CGM) devices, and more particularly, to optical couplers used to direct excitation light from a light-emitting diode (LED) into a fiber to illuminate or fluoresce a glucose binding protein (GBP) and then transmit the light emitted from the GBP to photodiode detectors.

BACKGROUND OF THE INVENTION

In patients with diabetes, glucose levels need to be monitored to maintain a healthy balance of glucose in the body. Glucose levels can be monitored by GBP coated sensors such as on-body CGM devices. On-body CGM devices generally include a light source used to illuminate or fluoresce GBP within a patient. These devices capture the light subsequently emitted by the GBP and analyze band wavelengths of the emitted light to determine the level of GBP. To identify GBP levels, a comparison can be made between the power of a reference band and the power of a signal band, which are both components of the light emitted by the GBP. The ratio of power of the reference band and the signal band is typically substantially proportional to the proportion of or level of glucose in the body of a patient.

Capturing and measuring the reference and signal bands of light emitted by a GBP has been accomplished by use of a series of lens and filters, which direct light to the GBP and attempt to separate the reference and signal bands prior to, or at a photodiode.

For example, existing CGM device designs attempt to capture the entire spectrum of light emitted by the GBP by both a reference photodiode and a signal photodiode. Each photodiode must then filter or block either the reference band or the signal band to accurately analyze GPB levels. As a result, less light is detected overall, because the light in the signal band that illuminates the reference band photodiode will not be detected, and the light in the reference band that illuminates the signal band photodiode likewise will not be detected. This inefficiency can dilute the analysis of the band wavelengths and can require greater initial light emission from a light source, requiring more energy and battery life.

Another prior CGM device design utilizes three separate glass filter components that must be individually placed and aligned during assembly to accurately reflect and transmit light from a light source to the GBP and from the GBP to a photodiode. This use of three distinct glass filters can add manufacturing and assembly costs and can increase the possibility of failure due to improper alignment of the glass filters. The use of three glass filter can also increase the overall size of the CGM device making it more inconvenient and uncomfortable for a user.

Another prior CGM design uses multiple filters positioned over a significant distance with respect to one another to direct the reference and signal bands to two different photodiodes. This filter configuration can lead to higher levels of stray light that is lost during transmission, thereby increasing light efficiency and decreasing the accuracy of the photodiode detecting the signal and reference bands.

With the CGM device designs above, there are concerns over light transmission inefficiencies, which contribute to the need for greater initial light emission, requiring greater power input/battery life. Additional concerns include manufacturing costs associated with the assembly of multiple components and the significant overall size of the CGM device.

SUMMARY OF THE INVENTION

An aspect of embodiments of the present invention is to substantially address the above and other concerns, and provide improved CGM devices.

Another aspect of embodiments of the present invention is to provide an optical coupler configured to reduce the size of the CGM device and potential manufacturing costs.

Another aspect of embodiments of the present invention is to reduce light transmission inefficiencies which contribute to the need for greater initial light emission, thereby saving power and battery life.

Another aspect of embodiments of the present invention is to reduce the failure rate of the mass produced CGM devices by limiting the number of distinct components that need to be aligned with one another during assembly.

Another aspect of embodiments of the present invention is to provide a continuous glucose monitoring device that includes a light source for emitting light used to illuminate glucose binding protein (GBP). Light is emitted from the light source and reflected by an optical body and transferred to the GBP via a fiber. The GBP emits light via the fiber and the light is transmitted by the optical body. The light is separated by wavelength by at least one dichroic layer coupled to the optical coupler and transmitted to a corresponding photodiode.

The foregoing and/or other aspects of the present invention are achieved by providing a CGM device wherein an optical coupler is formed by a reduced number of distinct components and transmits light from a light source to a GBP and from the GBP to a photodiode while significantly reducing the amount of stray light, thereby improving the efficiency and accuracy of the CGM device.

The foregoing and/or other aspects of the present invention are achieved by providing an optical system including a first filter adapted to reflect light emitted from a light-emitting diode to illuminate a fluorescent body, and further adapted to transmit light emitted from the fluorescent body, and a second filter adapted to separate light transmitted by the first filter into signal band light and reference band light.

The foregoing and/or other aspects of the present invention are achieved by providing an optical system including a first filter adapted to reflect light emitted from a light-emitting diode to illuminate a fluorescent body, and further adapted to transmit light emitted from the fluorescent body, and a second filter adapted to separate light transmitted by the first filter into a first beam and a second beam.

The foregoing and/or other aspects of the present invention are achieved by providing an optical coupler comprising a fiber adapted to contact a fluorescent body, a light-emitting diode, a first filter adapted to reflect light emitted from the light-emitting diode to illuminate the fluorescent body through the fiber, and further adapted to transmit light emitted from the fluorescent body, a second filter adapted to separate light transmitted by the first filter into signal band light and reference band light, and a photodiode adapted to receive at least one selected from the set consisting of signal band light and reference band light transmitted by the second filter.

Additional and/or other aspects and advantages of the present invention will be set forth in the description that follows, or will be apparent from the description, or may be learned by practice of the invention.

BRIEF DESCRIPTION OF THE DRAWINGS

The various objects, advantages and novel features of illustrative embodiments of the present invention will be more readily appreciated from the following detailed description when read in conjunction with the appended drawings, in which.

DETAILED DESCRIPTION OF ILLUSTRATIVE EMBODIMENTS

Figure 1:
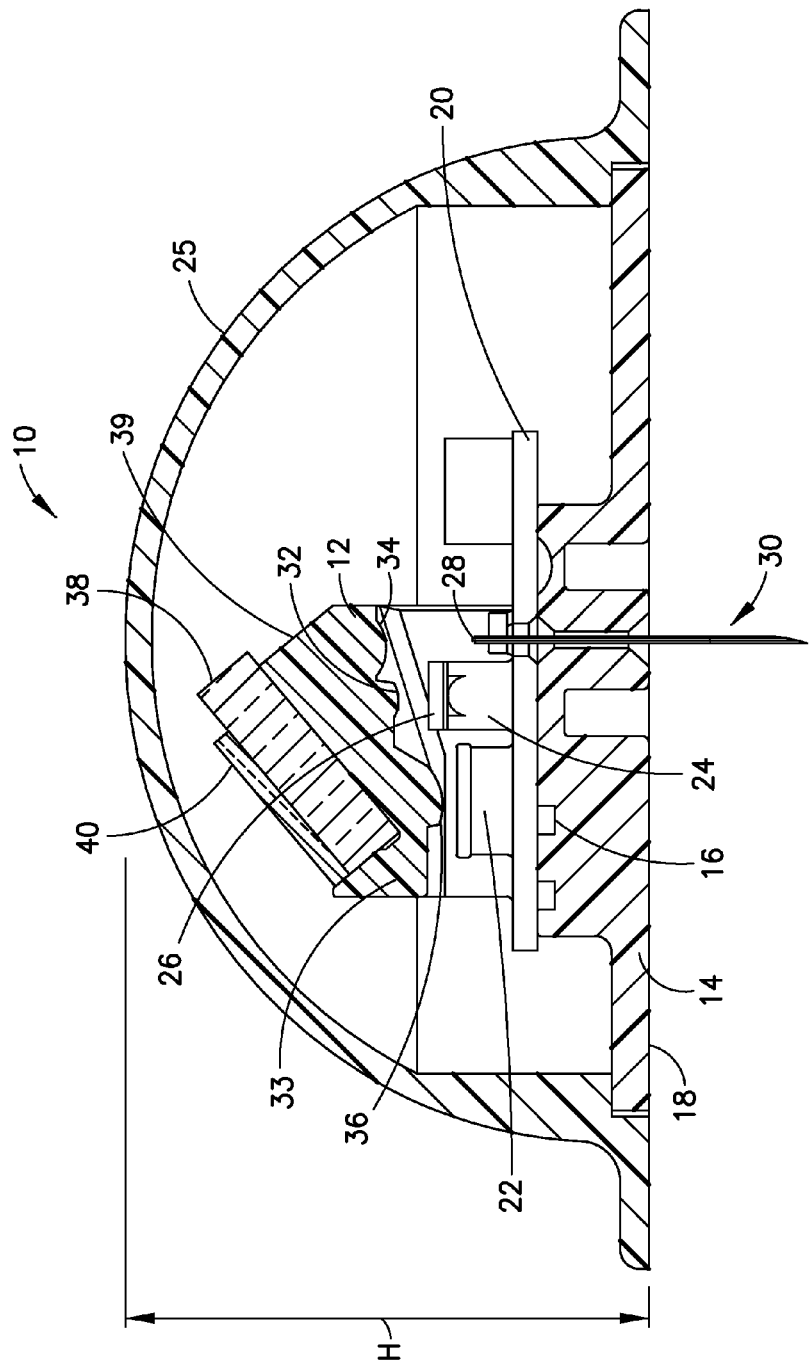
FIG. 1 is a cross-sectional view of a CGM device in accordance with an illustrative embodiment of the present invention.
Figure 2:
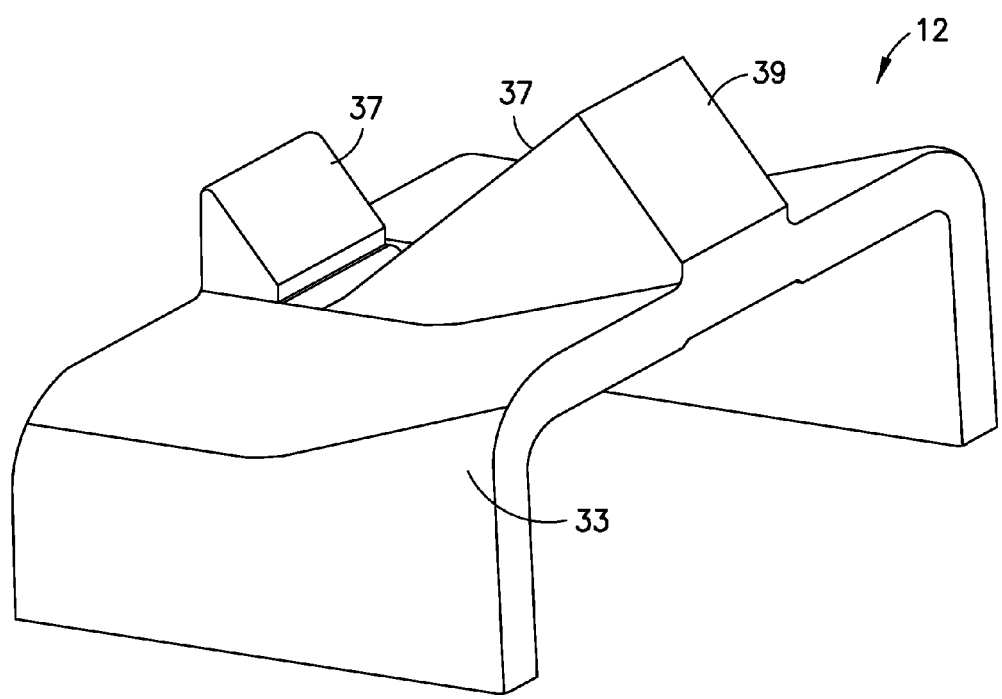
FIG. 2 is perspective view of an optical body of the CGM device of FIG. 1.

As will be appreciated by one skilled in the art, there are numerous ways of carrying out the examples, improvements and arrangements of CGM devices disclosed herein. Although reference will be made to the illustrative embodiments depicted in the drawings and the following descriptions, the embodiments disclosed herein are not meant to be exhaustive of the various alternative designs and embodiments that are encompassed by the disclosed invention.

In an illustrative embodiment according to the present invention, a continuous monitoring device is used in identifying an analyte, such as glucose in blood or interstitial fluid (ISF), using a biomaterial, such as glucose binding protein (GBP), that is brought into contact with the analyte. The continuous monitoring device includes a light source for emitting light used to illuminate the biomaterial. Light is emitted from the light source and reflected by an optical coupler and transmitted to the biomaterial via a fiber. The biomaterial emits light via the fiber and the light is transmitted by the optical coupler. The light is then separated by predetermined wavelength ranges by at least one dichroic layer coupled to the optical coupler and transmitted to a corresponding photodiode.

FIG. 1 illustrates an illustrative embodiment of an on-body CGM sensor 10 utilizing an optical coupler 12. The CGM sensor 10 includes a base 14 with a top surface 16 that supports the various components of the CGM sensor 10. A bottom surface 18 of the base 14 is used to support and adhere the CGM sensor to the skin of a user. A printed circuit board 20 is fixed to the top surface 16 of the base 14 and selectively controls power to a photodiode 22 and an LED 24, respectively fixed thereon. A cover 25 substantially encloses the components of the CGM sensor 10 and is fixed to the base 14.

The LED 24 emits light that is selectively filtered by a filter 26 fixed to a top surface of the LED 24. The optical coupler 12 is positioned above the LED 24 and photodiode 22 and directs the light emitted from the LED 24 into a fiber 28 positioned adjacent to the LED 24. The fiber 28 runs through the length of a needle 30. The needle 30 is used to insert the fiber 28 into a user to provide contact between the fiber 28 and biomaterial, such as GBP, beneath the skin of the user. The GBP coats or is deposited on the end of the needle 30 and contacts blood or interstitial fluid (ISF) after insertion into the user.

The optical coupler 12 includes a plastic connector 33 having three integral lenses, an LED lens 32, a fiber lens 34 and a detector lens 36. The plastic connector also includes a pair of inclined glass mounting surfaces 37 and a mirrored surface 39 that reflects light emitted from the LED 24 through the fiber lens 34 and into the fiber 28 to transmit light to the GBP. The glass mounting surfaces 37 are configured to support and fix filters at a predetermined angle with respect to the photodiode 22, the LED 24 and the fiber 28. The plastic connector 33 can be manufactured as a single injection molded component, reducing the number of individual parts of the optical coupler 12 that need to be manufactured and assembled. The plastic connector 33 can also be formed by other desired manufacturing processes capable of forming a single unitary component.

The optical coupler 12 includes a first glass filter 38 and a second glass filter 40. The first glass filter 38 is fixed to the second glass filter 40 via gluing or another desired securing mechanism. The glued first and second glass filters 38 and 40 are also fixed or glued to the inclined glass mounting surfaces 37. After the first and second glass filters 38 and 40 are fixed together, only two components need to be positioned during assembly, the fixed glass filters 38 and 40 and the inclined surfaces of the 37 of the optical coupler 12. This simplified assembly reduces possible misalignment of components and potential failure of the CGM sensor 10. Additionally, by fixing the first and second glass filters 38 and 40 together and then directly fixing them to the inclined surfaces of the optical coupler 12, less light is lost and/or diffused during operation, thereby improving the efficiency of the optical coupler 12, as opposed to other known optical couplers that require the light to travel in and out of more open air spaces which cause increased inefficiency in light transfer.

The first glass filter 38 includes a first dichroic filter coating 42 on the surface of the glass filter 38 mounted to the glass mounting surfaces 37. The first dichroic filter coating 42 reflects the light wavelengths emitted by the LED and transmits emission light wavelengths emitted from the GBP via the fiber 28.

The second glass filter 40 includes a second dichroic filter coating 44 on the same surface that is mounted to the first glass filter 38. The second dichroic filter coating 44 reflects shorter emission wavelengths representing a signal band and transmits longer wavelengths representing a reference band. A mirror surface 46 is formed on the surface of the second glass filter 40 opposite to the surface mounted to the first glass filter 38. The mirrored surface 46 reflects all wavelengths, but is particularly used to reflect the long wavelengths transmitted by the second dichroic filter coating 44.

Figure 3:
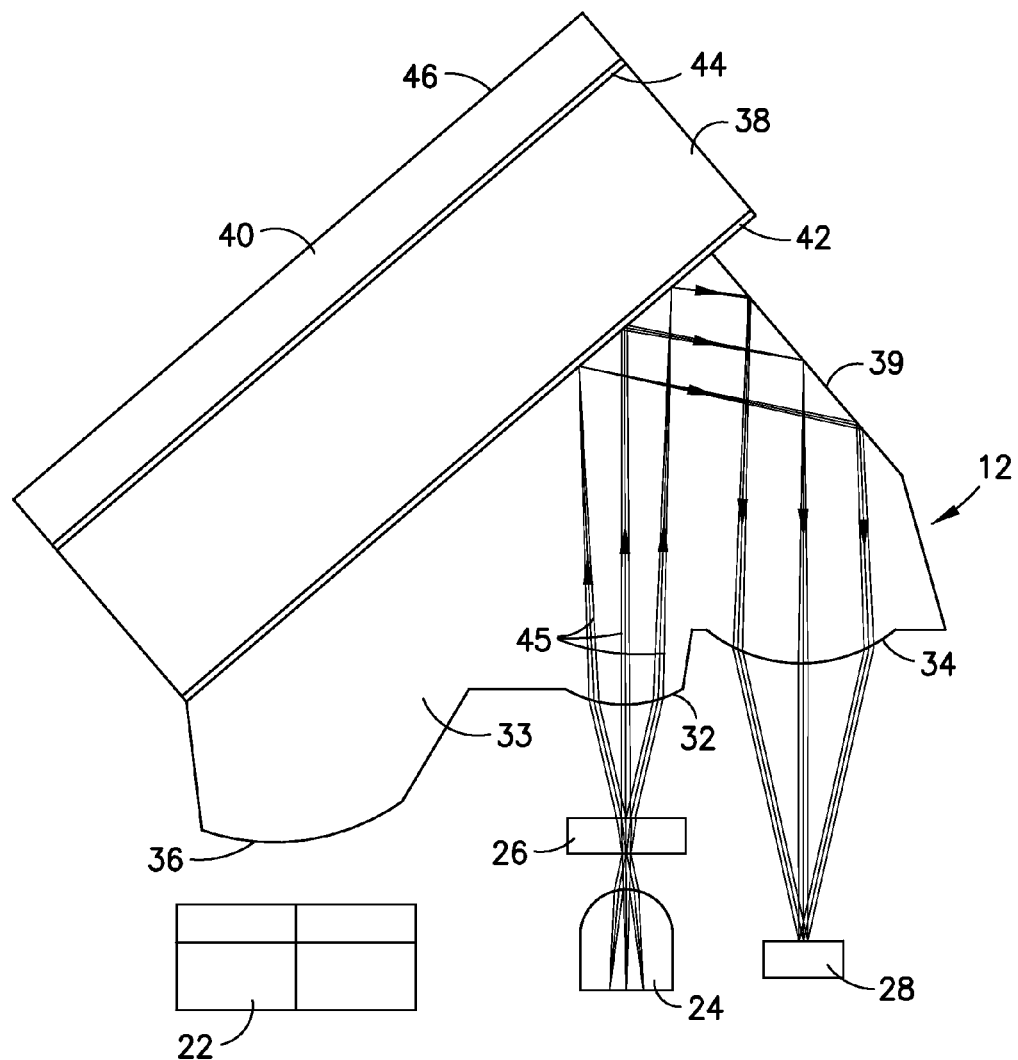
FIG. 3 is a schematic diagram of the CGM device of FIG. 1 including ray traces through an optical coupler, from an LED to a fiber face.

FIG. 3 illustrates a schematic diagram of the CGM sensor 10, including ray traces representing the light path from the LED 24 through the optical coupler 12 to the fiber 28 for illuminating the GBP in contact with an end of the fiber 28. Light 45 is first emitted from the LED 24 and filtered by the filter 26. The light 45 then travels through the LED lens 32 which focuses and directs the light 45 toward the first dichroic coating 42 which reflects the light 45 toward the mirrored surface 39 of the optical coupler 12. The mirrored surface 39 then reflects the light 45 toward the fiber lens 34 which focuses and transmits the light 45 toward the fiber 28 which illuminates the GBP (not shown).

Figure 4:
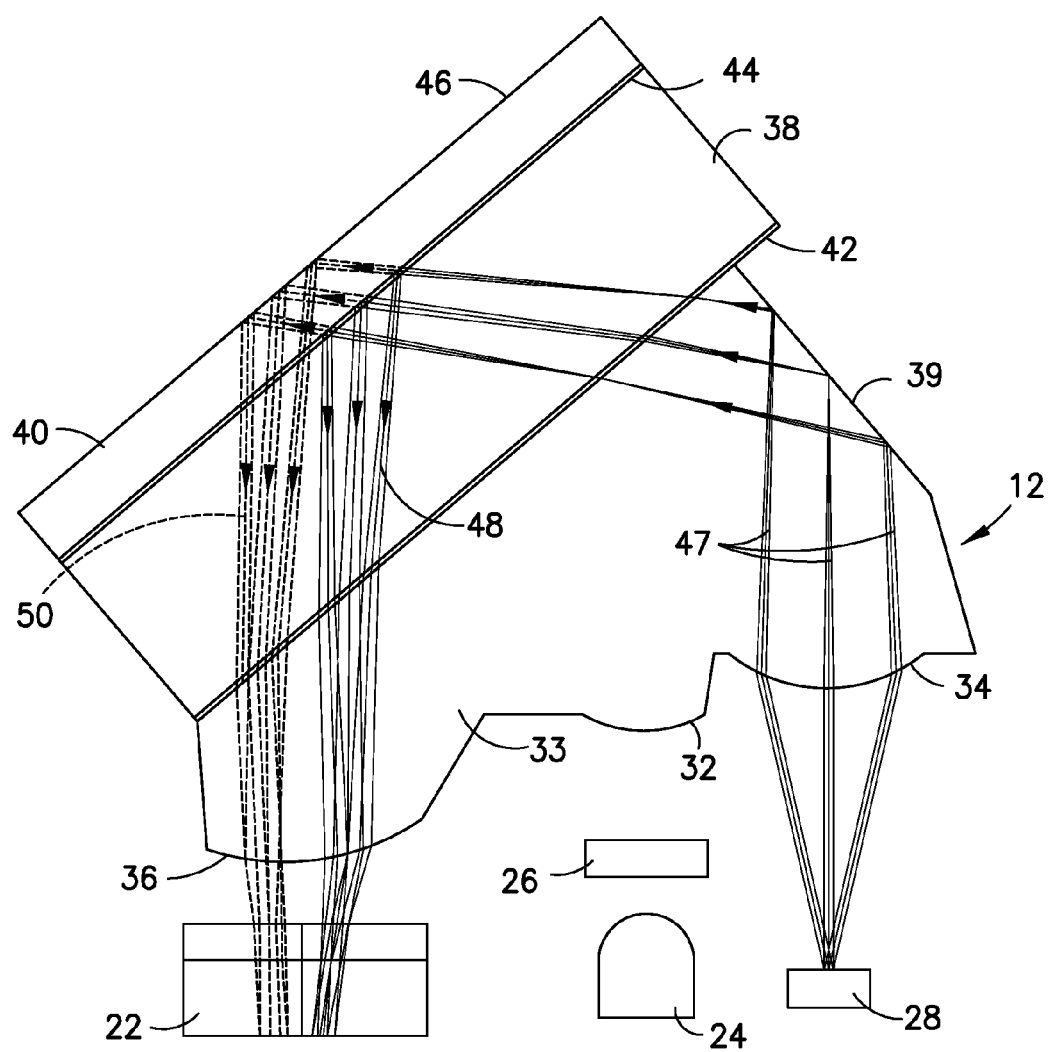
FIG. 4 is a schematic diagram of the CGM device of FIG. 1 including ray traces through the optical coupler, from the fiber face to a photodiode.

FIG. 4 illustrates a schematic diagram of the CGM sensor 10, including ray traces representing the light path from the fiber 28 through the optical coupler 12 to the photodiode 22 for capturing the reference band and the signal band wavelengths. Light 47 is emitted from the GBP through the fiber 28 and transmitted toward the fiber lens 34. The light 47 then travels through the fiber lens 34 which focuses the light 47 and directs it toward the mirrored surface 39 which reflects the light 47 toward the first dichroic coating 42 which transmits the light 47 toward the second dichroic coating 44.

The first dichroic coating 42 can be configured to filter the light 47 emitted by the GBP by reflecting only desired wavelengths and transmitting only the wavelengths that make up the signal and reference band wavelengths 48 and 50. The second dichroic coating 44 can be configured to further filter the light 47 by reflecting only the wavelengths of the signal band and transmitting all other wavelengths.

The signal band wavelength 48 reflects off the second dichroic coating 44 and passes at an angle through the first glass filter 38 and optical coupler 12. The signal band wavelength 48 is then focused by the detector lens 36 onto the photodiode 22.

After the signal band wavelength 48 is reflected off the second dichroic coating 44, only the reference band wavelength 50 remains, due to the filtering that occurs at the first dichroic coating 42. The reference band wavelength 50 is transmitted toward the mirrored surface 46 on the back surface of the second glass filter 40 which reflects all remaining wavelengths due to total internal reflection, or by having a silvered surface, which would also provide total reflection of remaining wavelengths. Alternatively, additional discrimination of the reference band wavelengths can be provided by replacing the mirrored surface 46 with a selective mirror coating that will only reflect the light in the reference band.

The light of the reference band continues back through the second glass filter 40 and passes through the first glass filter 38 and re-enters the optical coupler 12 and is focused by the detector lens 36 onto the photodiode 22.

Fixing the first and second glass filters 38 and 40 directly to the inclined surfaces 37 of the optical coupler 12 not only increase light transfer efficiency, but also reduces the size and height H of the CGM sensor 10. Due to the placement of the CGM sensor 10 directly onto a user during operation, reducing the size and particularly the height H of the CGM sensor 10 is greatly preferred to increase the comfort of the user during use.

Figure 5:
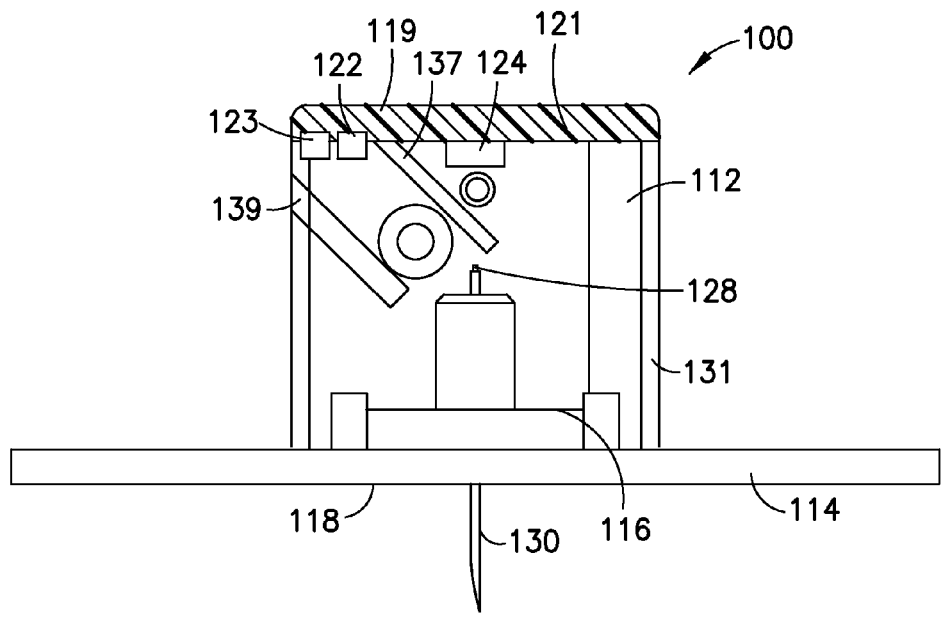
FIG. 5 is a cross-sectional view of a CGM device in accordance with another illustrative embodiment of the present invention.
Figure 6:
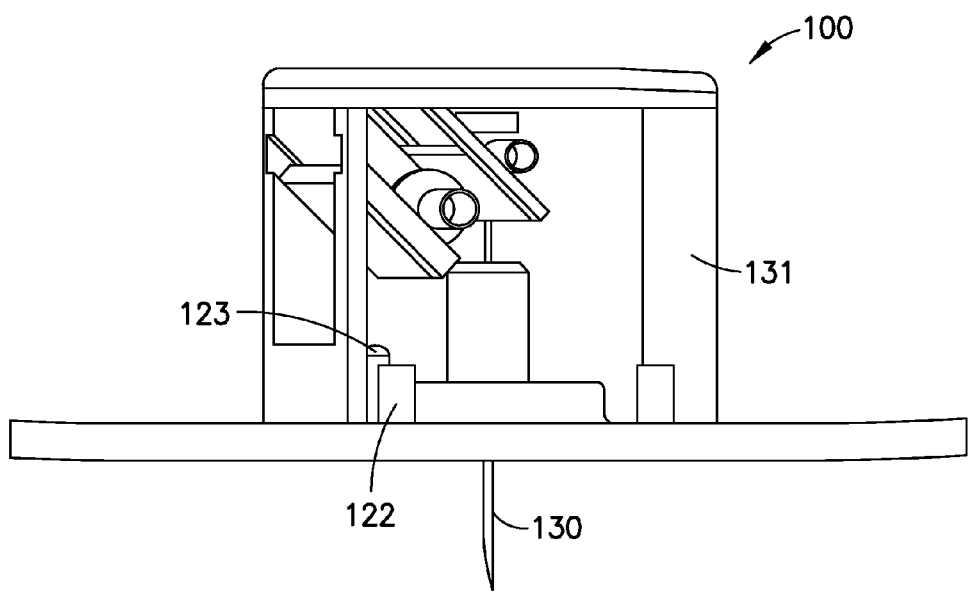
FIG. 6 is a side perspective view of the CGM device of FIG. 5.
Figure 7:
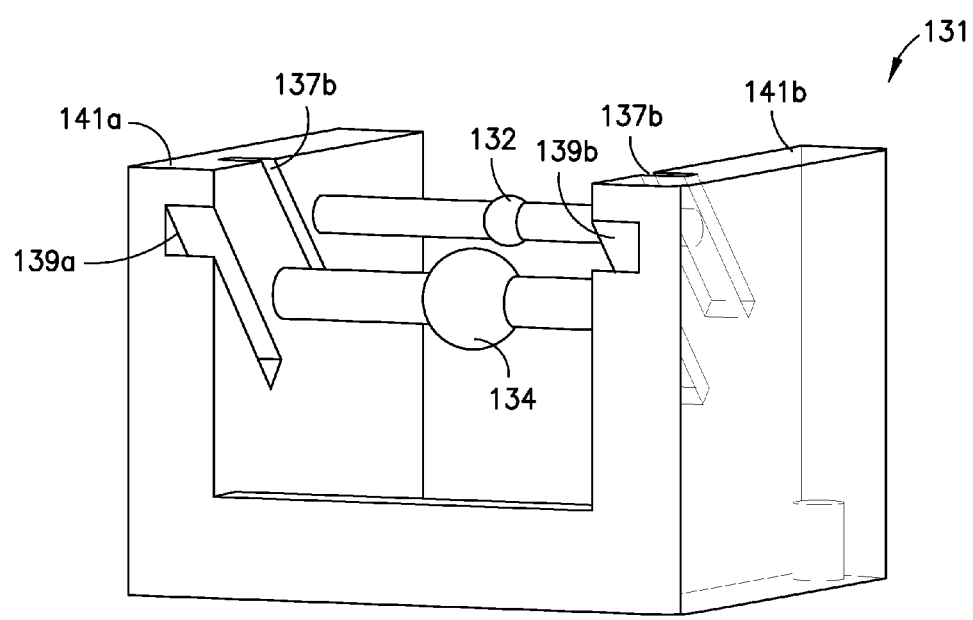
FIG. 7 is a rear perspective view of the CGM device of FIG. 5 with first and second dichroic filters removed.

FIGS. 5-7 illustrate an illustrative embodiment of an on-body CGM sensor 100 utilizing an optical coupler 112. The CGM sensor 100 includes a base 114 with a top surface 116 that supports a fiber mounting member 127 and a fiber 128. A bottom surface 118 of the base 114 is used to support and adhere the CGM sensor 100 to the skin of a user.

The fiber 128 runs through the length of a needle or catheter 30. The needle 130 is used to insert the fiber 128 into a user to provide contact between the fiber 128 and a biomaterial, such as GBP, beneath the skin of the user.

The CGM sensor 100 also includes an upper housing 119 fixed to the optical coupler 112 opposite to the base 114. The upper housing 119 provides a mounting surface 121 for mounting an LED 124 and a first and second photodiode 122 and 123.

The optical coupler 112 includes a plastic connector 131 having two integral rod lenses, an LED lens 132, a fiber lens 134. The plastic connector 131 also includes first pair of inclined slots 137a and 139a in a first vertical wall 141a and a second vertical wall 141b having a second pair of inclined slots 137b and 139b opposite to and corresponding to the first pair of inclined slots 137a and 139a. Inclined slots 137a and 137b fix a first glass filter 138 in a specific angled position with respect to the LED 124 and the fiber 128. Similarly, inclined slots 139a and 139b fix a second glass filter 140 in a specific angled position with respect to the fiber 128 and the photodiodes 122 and 123.

The plastic connector 131 can be manufactured as a single injection molded component, reducing the number of individual parts of the optical coupler 112 that need to be manufactured and assembled. The plastic connector 131 can also be formed by other desired manufacturing processes capable of forming a single unitary component. Additionally, since the LED lens 132 and the fiber lens 134 are integrally formed with the plastic connector 131, there are fewer opportunities for misalignment of the lenses 132 and 134 during assembly of the CGM sensor 100.

Figure 8:
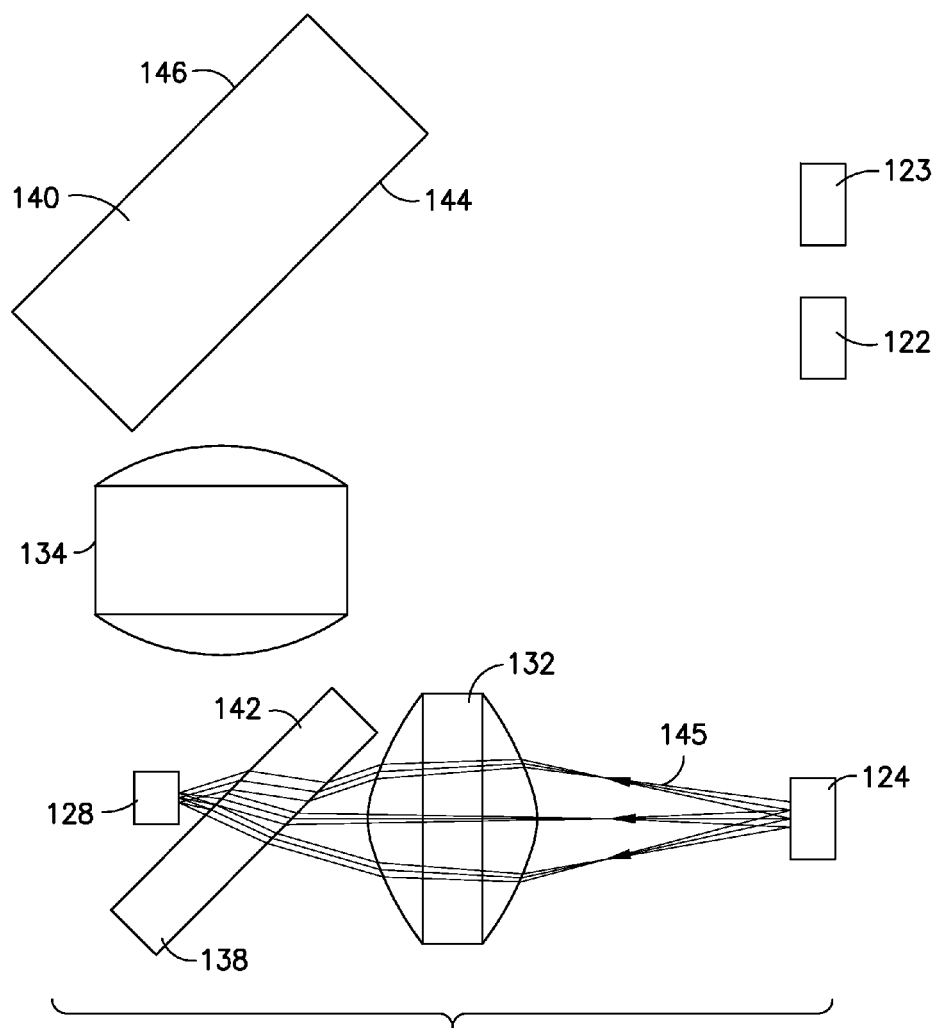
FIG. 8 is a schematic diagram of the CGM device of FIG. 5 including ray traces through the optical coupler, from a LED to a fiber face.

FIG. 8 illustrates a schematic diagram the CGM sensor 100, including ray traces representing the light path from the LED 124 to the fiber 128 for illuminating the GBP in contact with an end of the fiber 128.

Figure 9:
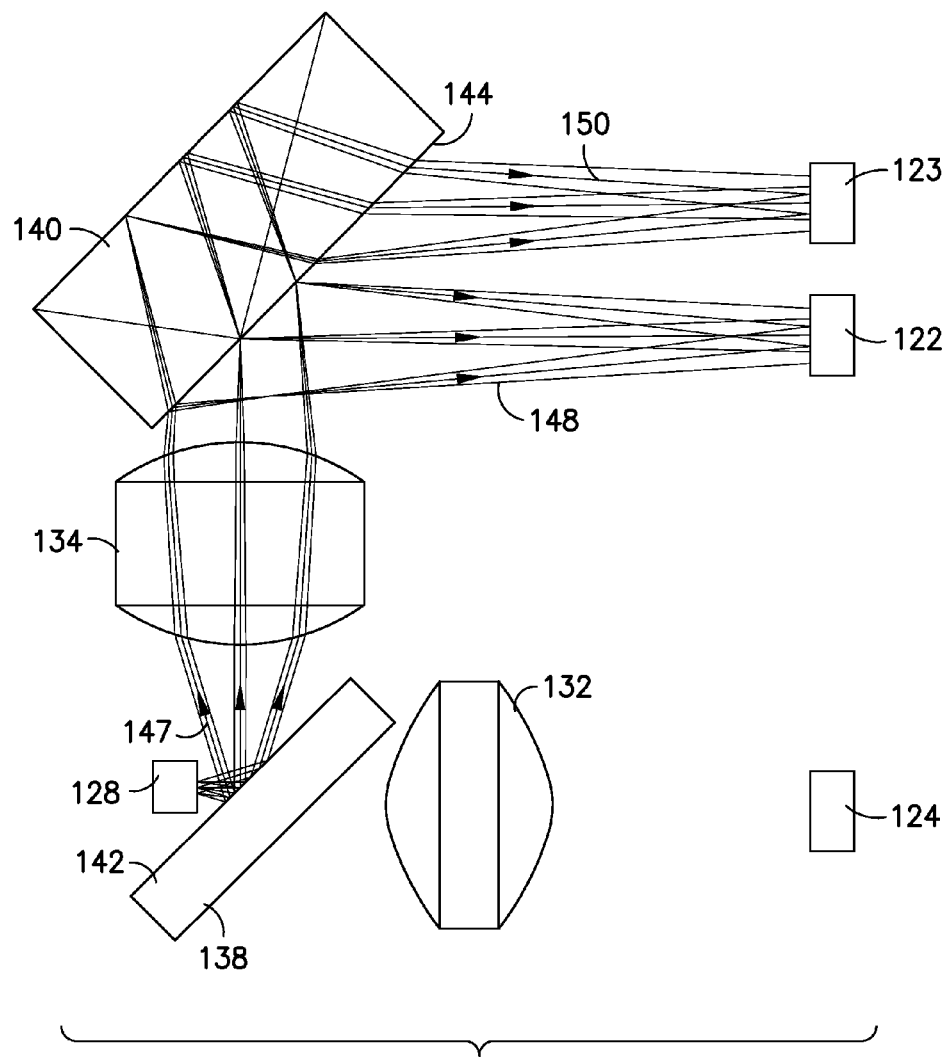
FIG. 9 is a schematic diagram of the CGM device of FIG. 5 including ray traces through the optical coupler, from the fiber face to a photodiode.

FIG. 9 illustrates a schematic diagram of the CGM sensor 100, including ray traces representing the light path from the fiber 128 to the photodiodes 122 and 123 for capturing the reference band and the signal band wavelengths.

Light 145 emitted from the LED 124 is collected by the LED lens 132 and directed through the first glass filter 138 into the fiber 128 and into the GBP. The first glass filter 138 includes a dichroic coating 142 which transmits the shorter light 145 wavelengths of the LED 124 and reflects the longer light 147 wavelengths emitted by the GBP via the fiber 128.

Light 147 emitted via the fiber 124 is reflected by the dichroic coating 142 of the first glass filter 138 and directed through the fiber lens 134, which collects and focuses the light 147 toward the second glass filter 140. The second glass filter includes a channel separation dichroic coating 144 on a front surface of the second glass filter 140. The face of the dichroic coating 144 reflects the shorter or signal band wavelength 148 and transmits the longer or reference band wavelength 150. The signal band wavelength 148 is focused down onto the signal band photodiode 148. The reference band wavelength 150 is reflected by a reflective coating 146 on a rear face of the second glass filter 140 and passes through the dichroic coating 144 and is focused down onto the reference band photodiode 123.

Figure 10:
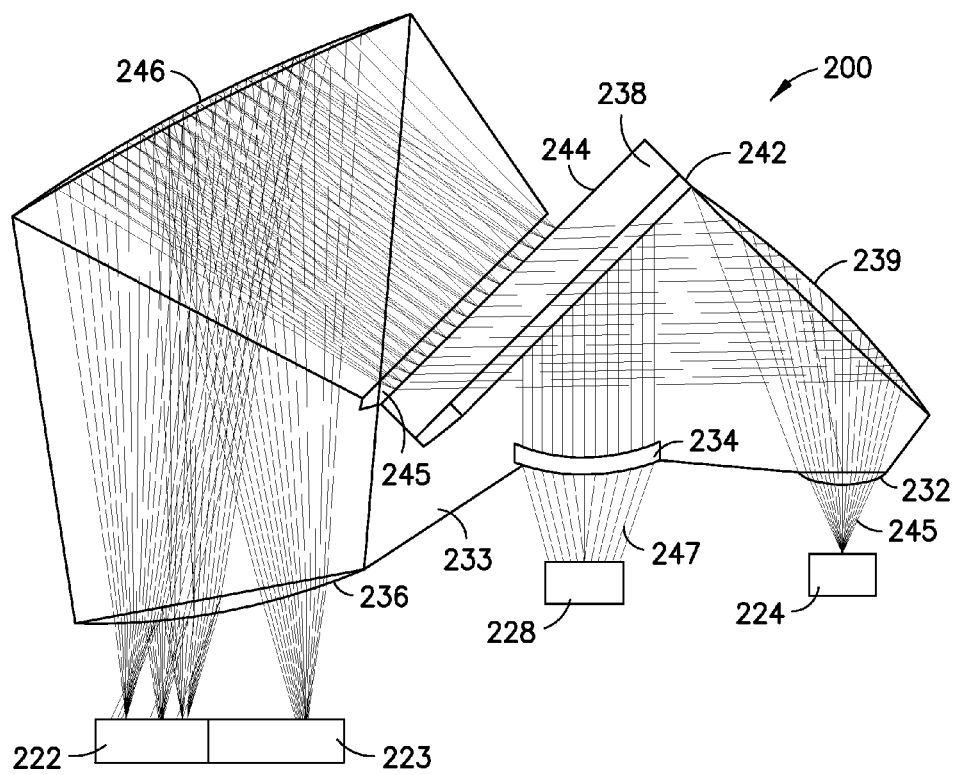
FIG. 10 is a schematic diagram of a CGM device of a further illustrative embodiment of the present invention, including ray traces through an optical coupler.

FIG. 10 illustrates a schematic diagram of another illustrative CGM sensor 200, including ray traces representing the light path from an LED 224 to a fiber 228 for illuminating the GBP and the light from the GBP to the photodiodes 222 and 223.

Light 245 is first emitted from the LED 224 to the LED lens 232 which focuses and directs the light 245 toward a reflective surface or coating 239 which reflects the light 245 toward a dichroic coating 242 on a front surface of a glass filter 238. The dichroic coating 242 is configured to reflect the light 245 toward the fiber lens 234 which focuses and transmits the light 245 toward the fiber 228 which illuminates the GBP in contact with the fiber 228.

After light 245 is absorbed by the GBP, light 247 is emitted from the GBP back through the fiber 228 and transmitted toward the fiber lens 234. The light 247 then travels through the fiber lens 234 which focuses the light 247 and directs it toward the dichroic coating 242 which is configured to transmit the light 247, falling within a predetermined wavelength range, emitted by the GBP and transmitting the light 247 through the glass filter 238 toward a diffraction grating layer 244.

The diffraction grating layer spreads the light 247 such that each wavelength has a different optical path after the diffraction grating layer 244. This enables the separation of all of the light for a reference band to be detected by the reference band 223 photodiode and all of the light for the signal band to be detected by the signal band photodiode 222. Alternatively, the dichroic coating 242 can also be configured to block wavelengths that do not fall within the signal or reference bands wavelength ranges. The diffraction grating layer 244 and the dichroic coating can be formed on opposing sides of the glass filter 238 that can be inserted into a slot in the plastic connector. The glass filter can be glued to the plastic connector via optical cement or other known optical adhesive. Gluing the glass filter 238 to the plastic connector 233 provides a single piece to be installed during final assembly of the CGM sensor 200.

After the light 247 passes through the diffraction grating 244 the light 247 passes through an air gap 245 and into the plastic connector 233. The light 247 is then reflected by reflection surface 246 of the plastic connector and is directed toward a photodiode lens 236 which collects and directs the light 247 to the corresponding photodiodes 222 and 223, or ASIC detectors.

Positioning the LED 224 away from the photodiodes 222 and 223 helps to cut down on the amount of stray light from the LED 224 that may adversely affect the sensitivity of the photodiodes 222 and 223. Additionally, the ordering and angling of the surfaces in the plastic connector 233 and the glass filter 238 also help to reduce stray light and enable greater overall efficiency of the CGM sensor 200 and enable a more compact design.

Figure 11:
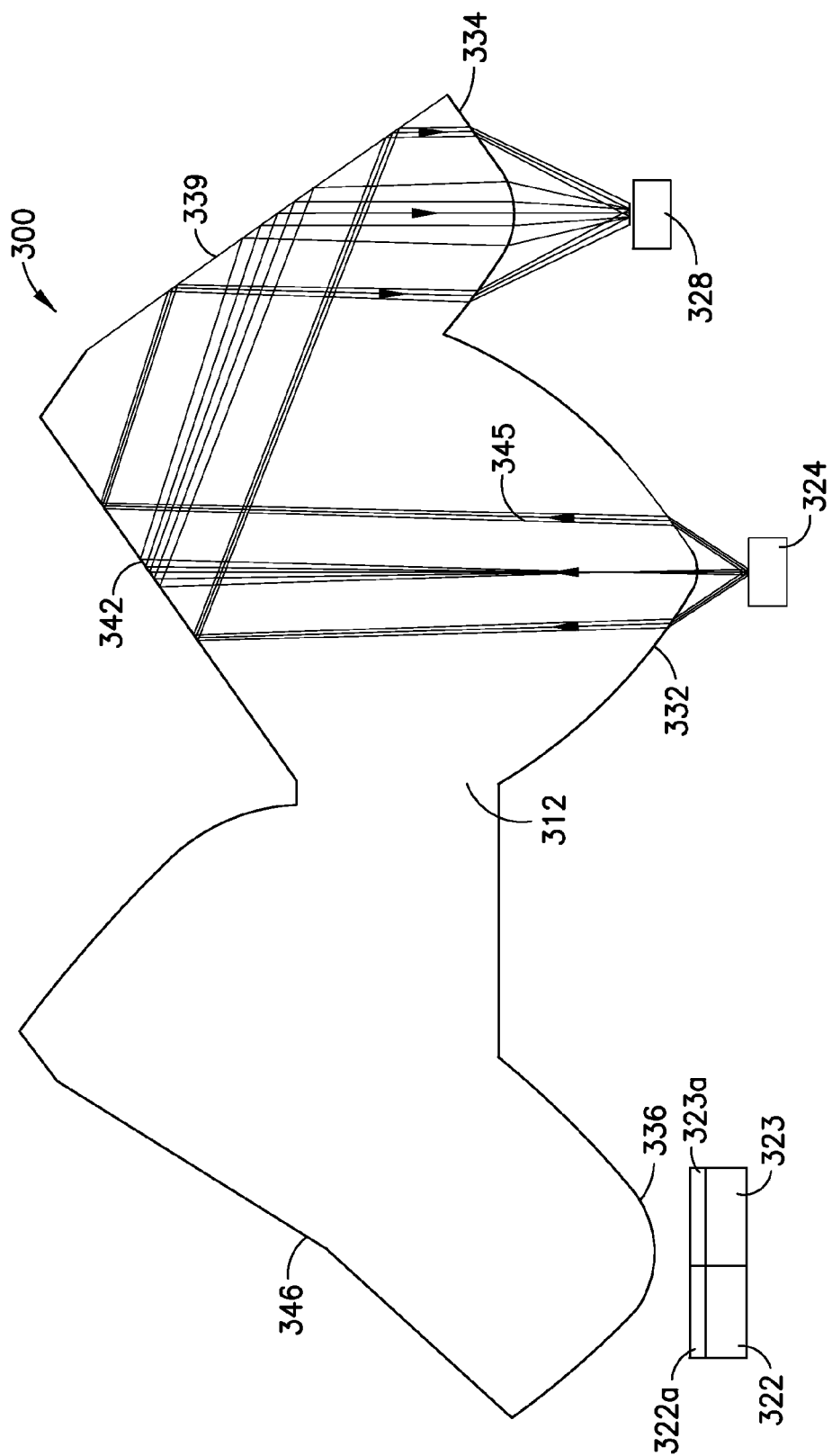
FIG. 11 is a schematic diagram of the CGM device of an additional illustrative embodiment, including ray traces through an optical coupler, from an LED to a fiber face.

FIG. 11 illustrates a schematic diagram of a further illustrative CGM sensor 300, including ray traces representing a light path from an LED 324 to a fiber 328 for illuminating GBP in contact with an end of the fiber 328.

Figure 12:
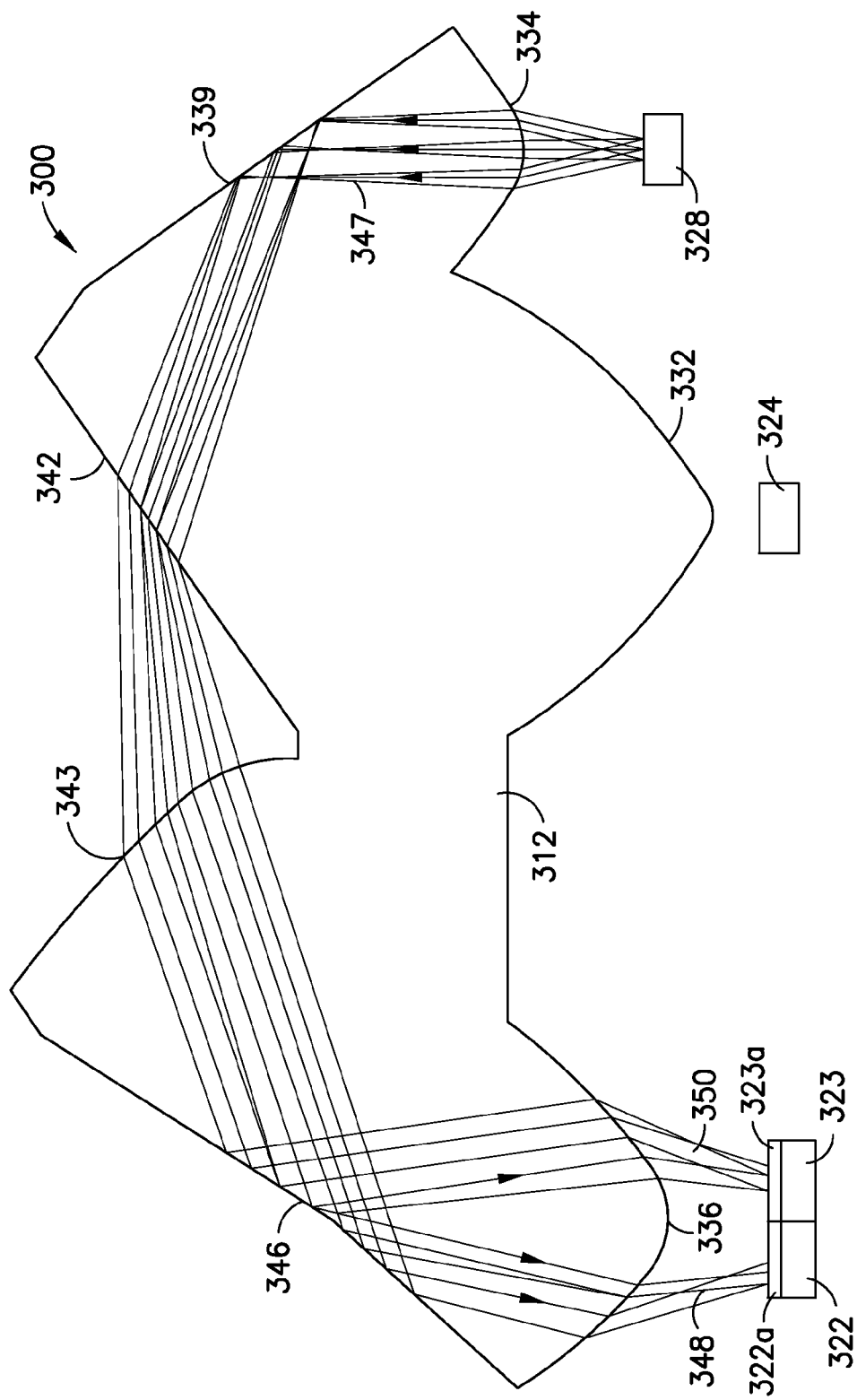
FIG. 12 is a schematic diagram of the CGM device of FIG. 11, including ray traces through the optical coupler, from the fiber face to a photodiode.

FIG. 12 illustrates a schematic diagram of the CGM sensor 300, including ray traces representing a light path from the fiber 328 to photodiode pixels 322 and 323 for capturing the corresponding reference band and the signal band wavelengths.

The CGM sensor 300 includes a plastic connector optical coupler 312 having three integral lenses, an LED lens 332, a fiber lens 334 and a detector lens 336. The optical coupler 312 also includes a dichroic coating 342 which is configured to reflect light 345 emitted by the LED 324. Additionally, the optical coupler 312 includes a mirrored surface 339 that also reflects light emitted from the LED 324 through the fiber lens 334 and into the fiber 328 to transmit the light to the GBP. The optical coupler 312 can be manufactured as a single injection molded component, reducing the number of individual parts of the CGM sensor 300 that need to be manufactured and assembled. The optical coupler 312 can also be formed by other desired manufacturing processes capable of forming a single unitary component.

In operation, light 345 is emitted from the LED 324 and is collected by an LED lens 332 and directed toward the dichroic coating 342 that reflects the light 345 wavelengths of the LED 324. The light 345 is then directed to the mirrored surface 339, experiences total internal reflection, and is directed toward the fiber lens 334. The fiber lens 334 then focusses the light 345 from the LED 324 into the fiber 328 and to the GBP at the end of the fiber 328.

Light 347 from the GBP exits the fiber 328 and is collected by the fiber lens 334. The light 347 is reflected by the mirrored surface 339, passes through the dichroic coating 342 and refracts into adjacent air space. The light 347 then reenters the optical coupler 312 at a collimation lens 343 and is directed toward a faceted mirror surface 346. The light 347 is then reflected at the faceted mirror surface 346 due to total internal reflection and is divided substantially evenly into two beams 348 and 350, one reflecting from each facet of the mirror surface 346. The two beams 348 and 350 are then focused by the photodiode lens 336 with the first beam 348 directed to a first photodiode pixel 322 and the second beam directed to a second photodiode pixel 323, such that half of the light 347 reaches each pixel.

Each pixel 322 and 323 has a corresponding bandpass filter 322*a* and 323*a* integrated directly on top of the pixel 322 and 323. Pixel 322 has a bandpass filter 322*a* that passes only the wavelengths in a reference band and pixel 323 has a bandpass filter 323*a* that passes only the wavelengths in the signal band. Therefore, the optical coupler 312 does not need to provide any separation of the light 347 wavelengths because the pixels 322 and 323 each have their own, distinct filters. This eliminates the need for a glass filter to separate the light wavelengths, thus providing a single unitary component for manufacturing which reduces costs of manufacture and overall size of the optical coupler 312.

In the immediately preceding embodiment, a single filter coating is applied directly onto the plastic optical coupler 312 and the other filter coatings are applied directly onto the photodiode pixels 322 and 323, eliminating the need for any glass filters to be integrated with the optical coupler 312. Because the glass filters have been eliminated the overall height of the optic body can be reduced, for example, the CGM sensor 10 shown in FIG. 1 may have a height of approximately 6.5 mm, whereas the CGM sensor 300 may have a height of approximately 3 mm.

Although only a few illustrative embodiments of the present invention have been described in detail above, those skilled in the art will readily appreciate that many modifications are possible in the illustrative embodiments, and various combinations of the illustrative embodiments are possible, without materially departing from the novel teachings and advantages of this invention. Accordingly, all such modifications are intended to be included within the scope of this invention.

The invention claimed is:

1. An optical system comprising:
a first filter adapted to reflect light emitted from a light-emitting diode in a first frequency band to illuminate a fluorescent body, and further adapted to transmit light emitted from the fluorescent body in a second frequency band;
a second filter adapted to separate light transmitted by the first filter by reflecting a signal band light and transmitting a reference band light; and
a single optical connector comprising at least two integral lenses and an inclined surface upon which said first filter is mounted and said second filter is positioned to direct the reflected signal band light through the inclined surface.

2. The optical system of claim 1, further comprising a photodiode adapted to receive at least one selected from the set consisting of signal band light and reference band light transmitted by the second filter.

3. The optical system of claim 1, wherein the first filter comprises a first glass filter comprising a first dichroic filter coating on a first surface of the first glass filter,
wherein the first dichroic filter is adapted to reflect light emitted by the light-emitting diode and is further adapted to transmit light emitted from the fluorescent body.

4. The optical system of claim 1, wherein the first filter is further adapted to block wavelengths outside of a signal band wavelength range and a reference band wavelength range.

5. The optical system of claim 1, wherein the first filter comprises a glass filter coated by a dichroic filter coating.

6. The optical system of claim 1, wherein the second filter comprises a second glass filter comprising a second dichroic filter coating on a first surface of the second glass filter,
wherein the second dichroic filter is adapted to reflect light of wavelengths associated with a signal band, and is further adapted to transmit light of wavelengths associated with a reference band.

7. The optical system of claim 1, wherein wavelengths associated with the signal band are shorter than wavelengths associated with the reference band.

8. The optical system of claim 1, wherein the second filter comprises a diffraction grating layer adapted to spread light in accordance with wavelength of light.

9. The optical system of claim 1, wherein the first filter and the second filter are formed on opposing sides of a filter element.

10. An optical system comprising:
a first filter adapted to reflect light emitted from a light-emitting diode in a first frequency band to illuminate a fluorescent body, and further adapted to transmit light emitted from the fluorescent body in a second frequency band;
a second filter adapted to separate light transmitted by the first filter by reflecting a first beam of light in a signal band and transmitting a second beam of light in a reference band; and
a single optical connector comprising at least two integral lenses and an inclined surface upon which said first filter is mounted and said second filter is positioned to direct the first beam of light through the inclined surface, wherein the second filter is adapted to separate light transmitted by the first filter substantially evenly into the first beam and the second beam.

11. The optical system of claim 10, further comprising a photodiode adapted to receive at least one selected from the set consisting of the first beam and the second beam.

12. The optical system of claim 11, wherein the photodiode comprises a filter that blocks wavelengths outside of one selected from the set consisting of a signal band wavelength range and a reference band wavelength range.

13. The optical system of claim 12, wherein the filter comprises a filter coating.

14. The optical system of claim 10, wherein the first filter and the second filter are formed into a unitary component.

15. An optical coupler comprising:
a fiber adapted to contact a fluorescent body;
a light-emitting diode;
a first filter adapted to reflect light emitted from the light-emitting diode in a first frequency band to illuminate the fluorescent body through the fiber, and further adapted to transmit light emitted from the fluorescent body in a second frequency band;
a second filter adapted to separate light transmitted by the first filter by reflecting a signal band light and transmitting a reference band light;
a single optical connector comprising at least two integral lenses and an inclined surface upon which said first filter is mounted and said second filter is positioned to direct the reflected signal band light through the inclined surface; and
a photodiode adapted to receive at least one selected from the set consisting of signal band light and reference band light transmitted by the second filter.

16. The optical coupler of claim 15, further comprising:
an light-emitting diode lens adapted to focus emitted from the light-emitting diode toward the first filter;
a fiber lens adapted to focus light toward the fiber, and further adapted to focus light from the fiber; and
a detector lens adapted to focus light onto the photodiode.

17. The optical coupler of claim 16, wherein the light-emitting diode lens and the fiber lens are integrally formed.

18. An optical sensor comprising:
the optical coupler of claim 15; and
a base with a bottom surface and a top surface, wherein the bottom surface is adherable to skin,
wherein the light-emitting diode is disposed on the top surface of the base, and
wherein the photodiode is disposed on the top surface of the base.

19. The optical system of claim 15, wherein the fluorescent body comprises a biomaterial.

20. The optical system of claim 15, wherein the fluorescent body comprises a glucose binding protein.

* * * * *